United States Patent [19]

Davis et al.

[11] 4,297,749
[45] Nov. 3, 1981

[54] HEART VALVE PROSTHESIS

[75] Inventors: Robert B. Davis, Framingham; John Skelton, Sharon, both of Mass.; Richard E. Clark; Wilbur M. Swanson, both of St. Louis, Mo.

[73] Assignees: Albany International Corp., Albany, N.Y.; Washington University, St. Louis, Mo.

[21] Appl. No.: 125,121

[22] Filed: Feb. 27, 1980

Related U.S. Application Data

[63] Continuation-in-part of Ser. No. 790,442, Apr. 25, 1977, Pat. No. 4,192,020, which is a continuation-in-part of Ser. No. 771,359, Feb. 23, 1977, abandoned, which is a continuation-in-part of Ser. No. 575,438, May 7, 1975, abandoned.

[51] Int. Cl.³ .............................................. A61F 1/22
[52] U.S. Cl. ................................................... 3/1.5
[58] Field of Search ........................... 3/1.5, 1, 1.4

[56] References Cited

U.S. PATENT DOCUMENTS

| | | |
|---|---|---|
| 3,571,815 | 3/1971 | Somyk ........................ 3/1.5 |
| 3,608,097 | 9/1971 | Bellhouse et al. ............. 3/1.5 |
| 3,736,598 | 6/1973 | Bellhouse et al. ............. 3/1.5 |
| 3,755,823 | 9/1973 | Hancock ...................... 3/1.5 |
| 4,106,129 | 8/1978 | Carpentier et al. ........... 3/1.5 |
| 4,192,020 | 3/1980 | Davis et al. .................. 3/1.5 |

FOREIGN PATENT DOCUMENTS 158988  5/1964  U.S.S.R. ................................ 3/105

OTHER PUBLICATIONS

"Clinical Experience with Supported Homograft Heart Valve for Mitral and Aortic Valve Replacement", by S. Sugie et al., The Journal of Thoracic & Cardiovascular Surgery, vol. 57, No. 4, Apr. 1969, pp. 455-463.

"The Direct Approach for the Correction of Aortic Insufficiency", by Charles A. Hufnagel et al., J.A.M.A., vol. 178, No. 3, Oct. 21, 1961, pp. 275-279.

"Comparative Study of Some Prosthetic Valves for Aortic and Mitral Replacement", by Charles A. Hufnagel et al., Surgery, vol. 57, No. 1, Jan. 1965, pp. 205-210.

Primary Examiner—Ronald L. Frinks
Attorney, Agent, or Firm—Kenway & Jenney

[57] ABSTRACT

A frame system for heart valve prosthesis. A first frame has at least three generally parallel legs each comprising a pair of rod portions connected at one end and diverging at the other end as lobes respectively connecting with rod portions of others of said legs. The lobes form an aperture therebetween and the legs are adapted to receive the margin of a valve leaflet between the rod portions thereof. Thus, the leaflet may be secured to two adjacent legs and the interconnecting lobe so as to have a free edge extending between said adjacent legs. A second frame is adapted to nest with the first frame and comprises a rod formed to be substantially congruent with the interconnecting lobes, whereby the leaflets may be secured to and between the frames.

6 Claims, 11 Drawing Figures

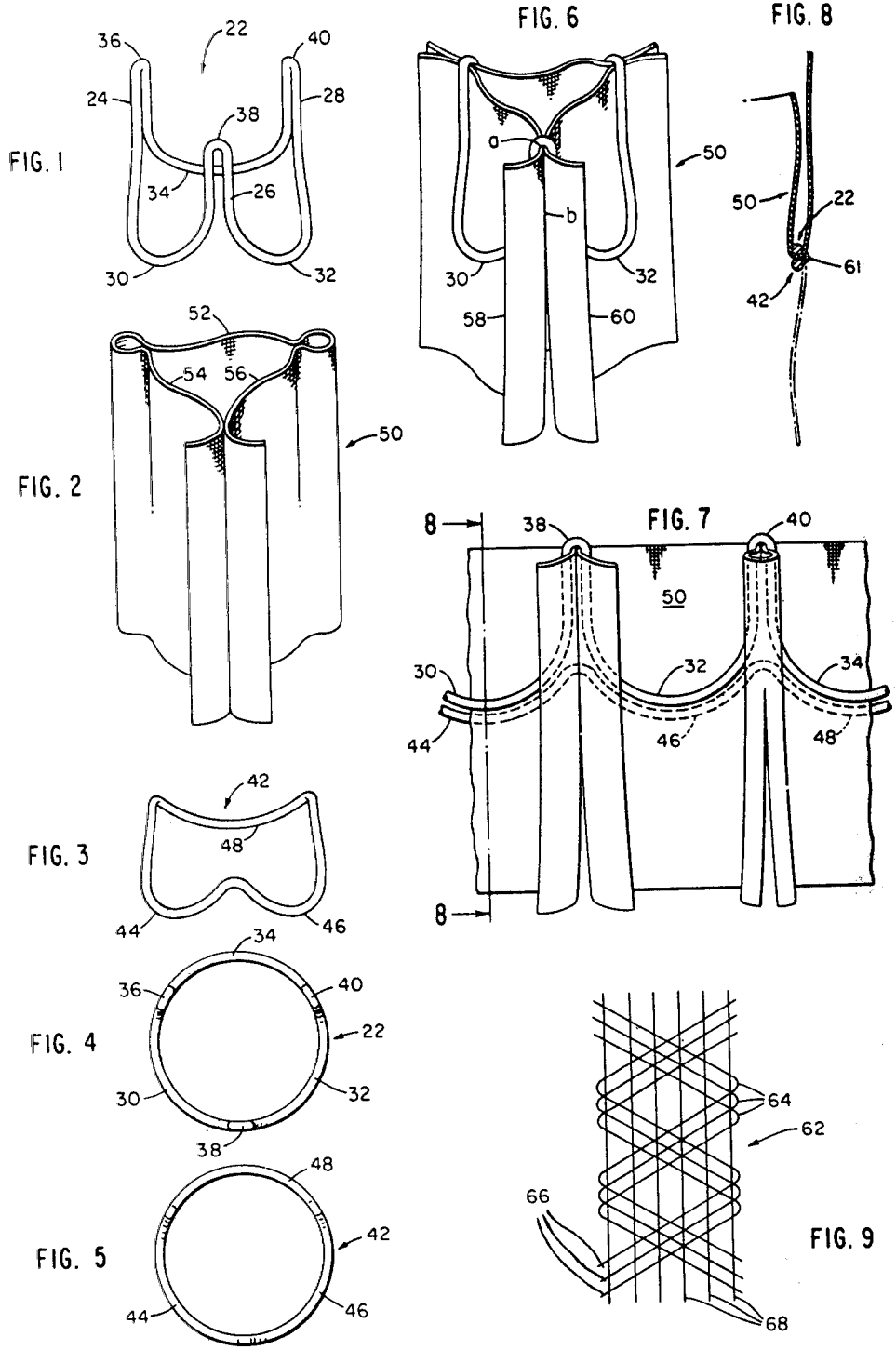

HEART VALVE PROSTHESIS

BACKGROUND OF THE INVENTION

The invention described herein was made in the course of work under a grant or award from the Department of Health, Education and Welfare.

This application is a continuation-in part of copending application Ser. No. 790,442, filed Apr. 25, 1977 by Robert B. Davis, John Skelton, Richard E. Clark and Wilbur M. Swanson, now U.S. Pat. No. 4,192,020, which is a continuation-in-part of abandoned application Ser. No. 771,359 filed Feb. 23, 1977 by Richard E. Clark, John Skelton and Robert E. Davis, said abandoned application being a continuation-in-part of Ser. No. 575,438, filed May 7, 1975 and now abandoned.

This invention relates generally to sheet materials for vascular, heart valve and other prosthetic implants. More particularly, it relates to such sheets fabricated of synthetic materials.

A principal object of this invention is to provide synthetic sheet materials having properties in use that closely approximate those of the natural tissues that they replace. For an understanding of these properties the human aortic valve may be taken as an example, in that it typifies properties that are required for other types of implants as well, such as vascular implants. This valve is of the leaflet type, having thin flexible membranes with a face to face thickness of about 0.06 cm that open 70 to 90 degrees from horizontal into the surrounding blood vessel (ascending thoracic aorta), and form three contiguous pouches held in close and leak-proof mutual contact by the pressure of the blood when in the closed configuration. Thus the membranes cause a minimum of disturbance to the flowing blood when in the open configuration, but move quickly when the blood pressure reverses (changes sign) to prevent regurgitation. A number of properties of the human valve may be identified, and these comprise the more specific objects of the present invention.

A first characteristic of the human aortic valve is that its response time is minimal. Thus it is an object of this invention to provide a synthetic sheet material that has a low resistance to motion of the leaflets in terms of both the inertial and elastic components of such resistance. In general terms, this is achieved by making the leaflets as light in weight and as flexible as possible consistent with the other mechanical requirements of the valve discussed below. This will enable the valve to pass quickly from the fully open state to the fully closed state when the pressure differential changes sign, leading to reduced energy losses in the flowing blood, and a minimum of undesirable regurgitation.

A second property of the human aortic valve is the effectiveness of the seal. Observations of this function reveal that the sealing of the valve is accomplished by the intimate conjugation of regions (referred to as the coaptation zone) close to the free edges of the valve leaflets. The effectiveness of the seal depends upon the degree of compliance of the leaflet in directions both parallel to its plane and transverse to that plane. The high transverse compliance allows the two contacting surfaces to form a more intimate conformal fitting at the coaptation zone, and the high in-plane compliance insures that the coaptation zone is sufficiently large to make an effective seal. Experience with synthetic valve leaflet implants has shown that these two forms of compliance are influenced by different factors. When such implants are employed, natural tissue is deposited or formed on the leaflet, and the nature of this natural tissue depends upon the nature and geometry of the synthetic material in use. The transverse compliance is controlled to a large extent by the mechanical properties of this tissue. In contrast, the in-plane compliance is controlled directly by the mechanical properties of the substrate synthetic material. Therefore, for suitable in-plane compliance it is an object of this invention to provide synthetic materials having longitudinal (i.e., tensile) compliance similar to that of the human leaflet. In addition, for adequate transverse compliance, additional criteria must be met with respect to the promotion of suitable natural tissue on the surface of the implant fabric.

A third property of the human aortic valve is the provision of adequate load bearing capacity. For a more detailed understanding of this property, a distinction may be made between the tensile compliance in the circumferential direction of the cusp, that is, the in-plane direction parallel to the free edge of the valve leaflet, and the tensile compliance in the radial direction of the cusp, that is, the in-plane direction perpendicular to the free edge. In either direction, the maximum working load level may be taken for practical purposes as approximately 150 gm/cm of leaflet width. This load exists in the closed configuration of the valve during the peak operating pressure in the arterial system. These requirements for adequate load bearing capacity would appear to impose properties different from those associated with the high compliance requirements previously described. However, the paradox is resolved in nature by the marked nonlinearity of the stress-strain characteristic of the natural leaflet material. At low loads the material has an extremely low modulus, thus ensuring both rapid response and good conformal fitting, but at a particular value of elongation (typically in the 10% to 20% region) the modulus undergoes a marked increase, with the result that the natural tissue can sustain high levels of loading without excessive subsequent elongation, gross geometric distortion or rupture.

Quantitatively, the foregoing features may be described as follows. In the circumferential direction the natural leaflet extends very readily with increased load until an elongation of 10% to 12% is reached at a load of 1 to 2 gm/cm of leaflet width. Upon further increase in the load, the resistance to further elongation increases greatly, and at the maximum working load level of 150 gm/cm width the modulus is approximately 3600 gm/cm width, which corresponds to a modulus expressed in classical engineering units of 850 pounds per square inch (p.s.i.). In the radial direction of the cusp, the region of easy extension with increased load continues up to approximately 20% elongation, at which the load is about two gm/cm width. Upon further increases in load the resistance to further elongation, though greater than in the initial region, is not as high as it is in the circumferential direction. The working load in this direction is not as firmly established as in the circumferential direction, but at a load of 150 gm/cm width the modulus is approximately 1000 gm/cm width (250 p.s.i.). Thus in each direction there is a transition between an initial region in which the modulus is of the order of 10 gm/cm width and the high load region in which the modulus is between 1000 and 3600 gm/cm width.

In view of the variations that occur in the tensile moduli of natural heart valve and vascular tissues, it is difficult to ascribe exact significance to the absolute values of the moduli described above. However, it appears that satisfactory performance of a synthetic prosthesis can be obtained if a modulus can be achieved which is within a factor of two of the natural leaflet values given above. Accordingly, it is preferred that the fabrics of this invention have a tensile modulus that is no greater than about 7200 gm/cm of leaflet width nor less than about 500 gm/cm of leaflet width up to a load of about 150 gm/cm of leaflet width.

In copending application Ser. No. 901,085, now U.S. Pat. No. 4,191,218, the property of nonlinearity in the natural valve leaflet material is generally described, and a synthetic leaflet material composed of multifilament polyester yarns is disclosed. To obtain the desired nonlinearity in the stress-strain characteristic, these yarns are subjected to compaction and shrinking to produce crimps in the yarns. The easy compliance of the crimped yarns at low stress levels results from the fact that the crimps are being straightened out; and the substantially higher tensile modulus exhibited at higher stresses results from the fact that the straightened yarns are being stretched.

Another property of the natural valve leaflet is its ability to maintain its original geometry and structural integrity through a large number of cycles of stress. For these purposes four times $10^9$ cycles may be taken as the pertinent criterion. Accordingly, it is an object of this invention to provide a sheet material that has a rapid and near-complete recovery from applied stress. The fatigue lifetime of a material that is subjected to cyclic stress and strain is influenced by the amount of non-recovered work (hysteresis loss) that is associated with the stress cycle. If there is rapid and substantially complete elastic recovery of the material from a cyclically applied stress, a longer fatigue lifetime will generally result. Further, it is desirable to provide a sheet material in which the applied stresses do not undergo a change of direction, as such a change tends to reduce the fatigue lifetime of most materials.

In addition to providing properties similar to those of natural heart valve leaflets, synthetic leaflets, vascular implants and the like must be so structured as to promote desirable tissue overlay when implanted, and the materials used must have adequate resistance to chemical change in the implanted environment.

SUMMARY OF THE INVENTION

According to this invention, sheet materials for cardiovascular and other prosthetic implants are fabricated of synthetic elastomers. These elastomers, when formed with appropriate geometrical configurations, exhibit all of the properties of the natural heart valve tissue previously described to a higher degree than those materials hitherto used. As used herein, elastomers are defined as polymeric materials that exhibit rubber-like elasticity characterized by low modulus (high compliance) and hence considerable elongation under low loads, with ultimate elongation reaching up to 1000% in some cases, with rapid recovery toward the original, unstretched dimension on removal of the stress, and with little or no permanent deformation as a result of the imposition of the stress. In polymeric materials of high molecular weight, this type of behavior is associated with a relatively small number of permanent crosslinks, and with rubber/glass transition temperatures considerably below the operating temperatures. The elastic extension in these materials is associated with the change in the configuration of the long polymer molecules from a randon coil in the unstretched state to the extended condition. The resistance to such a change increases as the molecules become increasingly aligned with the direction of stress, and the stress-strain curve usually shows an increase in slope as the elongation is increased. This is the type of elastic response that is needed to correspond with the response of the natural valve.

There are certain differences between the elastomers of this invention and the crimped fibers described in the abovementioned copending application. In the elastomers of this invention the nonlinearity in the stress-strain characteristic is produced at the molecular level; whereas, in the crimped fabrics described in said application the nonlinearity is imposed at the supramolecular, that is the fiber, level, being associated with the bending deformation of the crimped fiber. The process of unbending and rebending of the crimped filaments in the yarns is associated with cyclical stress reversals. These stress reversals due to this bending do not occur in the elastomers of this invention; therefore, an improvement in mechanical fatigue characteristics and a longer useful lifetime are achieved. Moreover, the elastomers of this invention differ from the polyester of said application in the higher modulus portion of the stress-strain curve. The differences here are exhibited by the relatively more rapid and more complete recovery of the elastomers when the stress is removed.

To achieve the desired minimal inertial and elastic resistance of the synthetic sheet material to the motions introduced by the hydrodynamic flow conditions, this invention involves the use of materials having a relatively low mass per unit area of the leaflet materials. Also, the second moment of area of the cross-section and the bending modulus of the material are of minimal magnitude. To attain these properties, a fabric of relatively small thickness is provided, subject to the attainment of an adequate level of load bearing capacity and filament durability.

For optimum performance the elastomeric sheet materials of the invention are also fabricated according to a number of other geometrical criteria. These criteria provide not only the above-mentioned properties in terms of thickness, compliance and stress-strain characteristics, but also the properties that relate to the promotion of desirable natural tissue layering upon the sheet material. Thus the sheet material is formed to provide a fibrous reticular face. Upon implantation, there is formed upon this face, because of its specific fibrous reticular nature, a satisfactory thin membranous deposit of endothelial cells, without an appreciable fibrous overgrowth of proteinaceous fibers such as collagen.

Suitable elastomeric sheet materials may comprise flat woven or braided yarns forming distributed foramina of appropriate maximum lateral aperture dimensions. Such foramina may be defined by the spacing between yarns or by the spacing between fibers within each yarn, or by both types of spacing. Other textile fabrication methods for producing a reticular fibrous sheet may be employed, for example knitting, flocking, needling, tufting, spun bonding, etc.

Additional features of this invention comprise certain geometrical and structural relationships which, when embodied in multifilament elastomeric yarns and fabrics, provide sheet materials that closely approximate the properties of natural heart valve leaflets and other natural tissues.

DRAWINGS

FIG. 1 shows the main frame of the preferred form of the heart valve.

FIG. 2 shows a fabric ribbon in the configuration formed by inserting it into the main frame between the rod portions of its legs.

FIG. 3 shows the second frame.

FIG. 4 is a top plan view of the frame shown in FIG. 1.

FIG. 5 is a top plan view of the frame shown in FIG. 3.

FIG. 6 shows the partially fabricated heart valve with the fabric inserted into the main frame and cut open preparatory to cementing thereto.

FIG. 7 is a developed view of the partially constructed heart valve, corresponding to FIG. 6.

FIG. 8 is a cross-sectional view taken on line 8—8 in FIG. 7.

FIG. 9 illustrates a flat braided fabric pattern.

DETAILED DESCRIPTION

Figure 10:
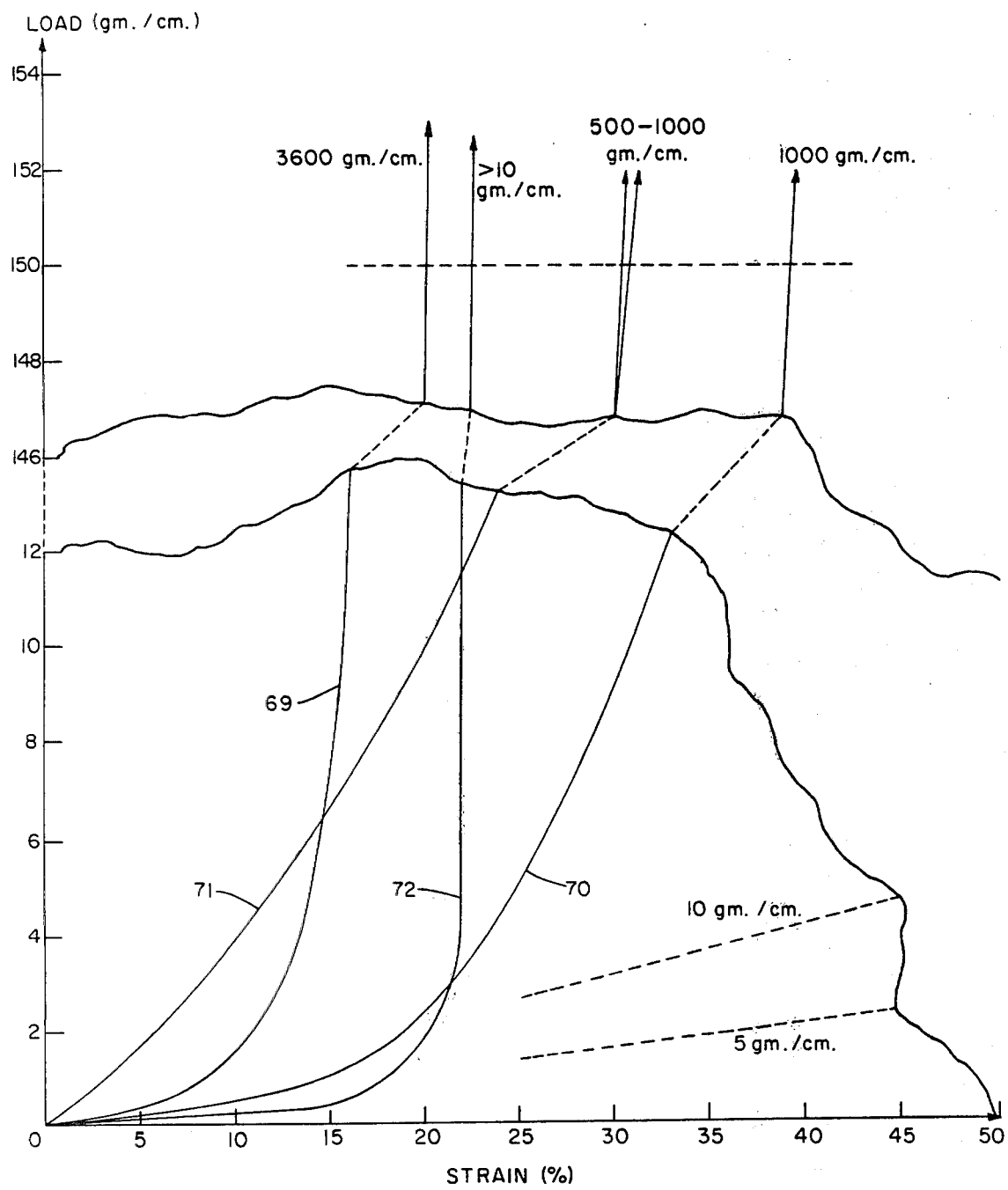
FIG. 10 is a stress-strain diagram comparing the characteristics of natural leaflet tissue, prior art woven synthetic implants, and elastomeric sheet material according to this invention.

FIGS. 1 to 8 show a preferred form of aortic trileaflet heart valve replacement. Referring to FIG. 1, there is shown a main frame 22 comprising a single length of 0.1 cm. diameter round polypropylene rod bent into a form having three mutually equidistant, generally parallel legs 24, 26 and 28, each leg comprising a pair of rod portions slightly spaced apart, the rod portions being connected at one end and diverging at the other end. The diverging rod portions form three lobes 30, 32 and 34. The connected ends of the rod portions in each pair form bights 36, 38 and 40. FIG. 4 is a top plan view of the main frame 22.

A second frame 42 (FIGS. 3 and 5) is formed of a single length of 0.1 cm. diameter round polypropylene rod bent into a form having three lobes 44, 46 and 48 generally congruent with the lobes 30, 32 and 34 so as to fit in close contact therewith as shown in FIG. 7.

The assembly is started by threading a ribbon 50 of elastomeric sheet material of the type hereinafter described, in this case a plain woven elastomeric fabric, through the three pairs of rod portions so as to produce the configuration shown in FIG. 2. The yarns of the fabric are multifilament yarns. The frame 22 is shown in FIG. 1 in exploded relation to FIG. 2 for clarity of illustration. The upper selvage has no uncut yarns and forms the free edges 52, 54 and 56 of valve leaflets.

Thus a double layer of the fabric is passed through each pair of rod portions forming one of the legs 24, 26 and 28. It is necessary to attach the fabric firmly to these legs, and also to the connecting lobes 30, 32 and 34. To facilitate this attachment, the fabric is preferably cut lengthwise externally of each leg as shown in FIG. 6. Referring to FIG. 6, adhesive such as polyurethane dissolved in tetrahydrofuran is applied to attach the fabric to each of the legs as follows. Flaps such as 58 and 60 are spread apart and the adhesive is applied at the external point of juncture of the flaps where they enter between the rod portions, in a continuous line extending between points a and b. The adhesive material reaches to the external surfaces of the frame by penetration through the fabric flaps along this line; that is, the adhesive contacts the rod portions of the frame only on their outer surfaces. The leaflets comprise only those portions of the fabric on the inside of the frame, and these portions are not penetrated by the adhesive. Thus local stiffening and resultant flex failure caused by such adhesive penetration is avoided.

The above method of adhesive application also distributes the stresses of flexure evenly along the margins of the leaflets, and avoids excessive stress concentrations. These margins are permitted to move upon each flexure over the rounded contours of the surfaces of the rod portions that are located on the inside of the frame, and that are not penetrated by the adhesive.

The attachment of the fabric to the lobes 30, 32 and 34 is next accomplished by first placing the second frame 42 adjacent these lobes with the fabric pieces passing therebetween as shown in FIGS. 7 and 8. Adhesive 61 is then applied through the fabric and to the surfaces of both the main frame 22 and the second frame 42, in a continuous line extending between the points b of the respective legs and connecting these three points. As in the previous step, the adhesive material preferably does not penetrate any portion of the leaflet material lying within the main frame 22, and remains out of contact with blood passing through the valve.

The foregoing steps essentially complete the fabrication of the leaflet portions of the valve. The remaining steps of fabrication are for the purpose of facilitating the suturing of the prosthesis within the heart. The excess fabric available on the outside of the frame can be rolled and consolidated along the junction line between the main and second frames to provide attachment points for stitches during surgical insertion.

The frame material is preferably polypropylene, although other materials have also been employed with success. Polypropylene has excellent flex endurance and chemical stability, but is difficult to attach by adhesive to other materials. To facilitate adhesion, the main and second frames 22 and 42 may be encapsulated with polyurethane by multiple dip coating. The resulting encapsulated frame components have proved to demonstrate the desired characteristics of polypropylene without structural failures or breakdowns at the adhesive junctures. Another preferred material of construction for the frame is the cobalt alloy sold under the trade designation "Elgiloy".

Valves employing the elastomeric fabric described herein have been tested in an accelerated fatigue tester to assess their long-term endurance characteristics. Fatigue failures so induced in prior art leaflet materials have generally occurred in the region of greatest fabric flexure, that is, along a line in each leaflet that is perpendicular to its free edge and substantially equidistant between the contiguous legs. The failures have generally occurred by breakdown of the filaments in the yarns running parallel to the free edge of the leaflets. As a means of providing greater fabric strength along the last-mentioned lines, woven fabrics may be provided with a greater number of load-bearing yarns in this direction. However, there is a limit to the increase that is possible using a plain woven pattern without seriously disturbing the geometry of the fabric interstices.

An alternative fabric construction pattern having improved strength against such fatigue failure is illustrated in FIG. 9. The fabric shown is a flat braided ribbon 62 comprising 3 sets of elastomeric yarns, namely, a first diagonal set 64, a second diagonal set 66 and a longitudinal inlaid set 68. The yarns in each of the three sets are preferably multifilament untwisted yarns. The ribbon 62 is braided on a conventional flat braiding machine. It will be noted that each selvage has uncut yarns and one of those becomes the free edge of each leaflet. Thus fraying of the free edges of the leaflets is avoided as in the example described above. In this embodiment both of the sets 64 and 66 perform the load-bearing function of a single set of yarns in the earlier-described fabric. The result is that a greater number of yarns have a significant component of load bearing capacity oriented parallel to the free edge.

The fabric 62 of FIG. 9 is preferably formed by braiding the yarn sets 64 and 66 with inlaid longitudinal yarns 68 in a well-known manner, thus producing a type of triaxial fabric. Such flat braided fabrics have an additional advantage over conventionally woven fabrics, in that they are inherently highly extensible in the cross machine direction, that is, in the direction perpendicular to the yarns 68. Such fabrics make it possible to produce a two-way stretch characteristic.

In the foregoing description, woven and braided fabrics have been described as embodied in replacement heart valve leaflets. However, many of the attributes of these fabrics as well as other textile sheet materials within the scope of this invention which have similar properties and are produced by such methods as knitting, flocking, needling, tufting, spun bonding, etc., make them ideally suited for other biomedical applications as well. For example, vascular prostheses, particularly those with small diameters, require a combination of good stretch characteristics and inherent biological inertness. In this case, fabrics essentially similar to any of those described herein may be woven, braided or otherwise fabricated in tubular form for use as conduits for flowing blood.

With either of the above tubular weave patterns, twoway stretch characteristics may be imparted to the vascular prosthetic devices. The radial compliance is particularly useful in avoiding stiffness mismatches at the boundaries between the existing artery and its synthetic replacement, particularly in small diameter arteries. A circumferential extension ratio of 1.5:1 is typically necessary in order to provide the proper match of properties, and this ratio has been provided by the above-described tubular materials.

We turn next to a description of the preferred fabrics for use in the above-described heart valve application and other prosthetic implant uses.

The preferred elastomers comprising the sheet materials of this invention are thermoplastic polyether esters prepared by transesterification from terephthalic acid, polytetramethylene ether glycol and 1,4-butanediol. These copolyesters possess a two-phase domain structure consisting of continuous and interpenetrating amorphous and crystalline regions. The amorphous elastomeric polyalkylene ether terephthalate soft segments contribute the elastomeric character to the polymer, whereas the crystalline tetramethylene terephthalate hard segments serve as thermally reversible tie points which are capable of holding the polymer chains together without the need for conventional covalent crosslinks. The synthesis of these copolymers is described in an article by G. K. Hoeschele, entitled "Segmented Polyether Ester Copolymers—A New Generation of High Performance Thermoplastic Elastomers," appearing in *Polymer Engineering and Science*, December, 1974, Vol. 14, No. 12. In the practice of this invention it is preferred to select those copolymers having relatively larger amounts of the soft segments as compared with the hard segments and specific examples tested have included the copolymers sold under the trademark Hytrel 4056 by E. I. du Pont de Nemours & Company (hereinafter called "Hytrel"). These exhibit exceptional low temperature flexibility, and when fabricated as multifilament yarns of suitable denier they can be woven or braided to produce fabrics having the desired properties.

Other elastomers that can be similarly fabricated are within the purview of the invention. These include (1) polybutylene terephthalate, (2) a block polyester polyurethane copolymer sold under the trademark "Pellethane" by Upjohn Company, (3) thermoplastic silicone block copolymer, and (4) a thermoplastic polyester elastomer sold under the trademark "Arnitel" by Akzo Plastics.

The foregoing elastomers are extruded as filaments using multiple orifice spinnerets in a conventional manner, and low-twist multifilament yarns are formed. These yarns are then woven or braided to form the prosthetic fabric, or otherwise fabricated into textile sheet material having the mechanical and structural properties hereinafter described.

The advantages of elastomeric materials include their relatively low tensile moduli at low levels of stress, as shown by FIG. 10. This figure illustrates the tensile stress-strain characteristics of the natural heart valve leaflet tissue and two synthetic yarn materials. Stress is measured in grams of tension force per centimeter of leaflet or fabric width and strain in percent of original length. Curve 69 represents the natural leaflet characteristic in the circumferential direction. Curve 70 represents the natural leaflet characteristic in the radial direction. Curve 71 is representative of a fabric formed with an elastomer according to this invention and specifically represents a fabric woven of Hytrel yarn. Curve 72 represents a fabric formed with a polyester, namely polyethylene terephthalate which has been microcrimped after weaving in the manner described in the above-mentioned copending application Ser. No. 901,085. By suitable microcrimping the fabric of curve 72 may be made to exhibit a low initial modulus up to a strain of about 20 percent, above which the crimps are straightened and the modulus is much higher. Either of curves 71 or 72 shows a modulus which is low enough at low levels of strain to perform satisfactorily in a heart valve prosthesis. However, as noted above, the low modulus properties are achieved in different ways.

As noted above, the elastomeric materials of the invention may be fabricated in any of several ways to form textile sheets having the described properties. The following description, as applied to the plain orthogonally woven embodiments in a heart valve implant, is illustrative.

Thickness

An important criterion of the woven fabric is its thickness. Preferably, this should not exceed approximately 0.06 cm, the thickness of the natural heart valve leaflet. In addition, if the fabric is composed of yarns each having eight or more filaments, the level of twist imposes a criterion as shown by the following expression:

$$4d \leq t \leq (2n)^{\frac{1}{2}}d \quad (1)$$

where "d" is the filament diameter or the minimum lateral dimension of the filament cross section where the latter is not circular but oval or otherwise of flattened shape, "t" is the fabric thickness, and "n" is the number of filaments per yarn. As used throughout this description "thickness" refers to a dimension at right angles to the plane of the fabric. (A separate criterion imposing an upper limiting value 12d is explained below under the heading "Flexural Rigidity".) The basis for expression (1) as applied to twist may be understood by reference to the following discussion.

The expression "4d" represents the minimum theoretical thickness of the woven fabric of multifilament yarns. This is attained when the warp and filling yarns are equally crimped during fabric production, as by weaving, and the yarns are sufficiently flattened by reason of having a low level of twist. The crimp here referred to is termed "structural crimp" and is distinguished from the crimp described in said application Ser. No. 901,085, which results from compaction and shrinking operations on the woven fabric. When the structural crimp is thus evenly distributed, the fabric thickness equals twice the thickness of a yarn; and the minimum theoretical thickness of a yarn having any degree of twist is twice the diameter of a filament, as required to accommodate the continuous filament relocation that is a necessary concomitant of the twisted structure.

On the other hand, if the yarns were highly twisted they would assume a more nearly circular shape, and the yarn thickness could be approximated by assuming that its cross section is a square made up of $n^{\frac{1}{2}}$ rows of filaments with $n^{\frac{1}{2}}$ filaments per row. In that case the fabric thickness would be approximated by the expression $2n^{\frac{1}{2}}d$. However, by reducing the level of twist the fabric thickness can be reduced, and the use of thin fabrics confers several benefits. The flexural rigidity of the fabric is reduced, as are the bending stresses and strains in the material; the fabric weight per unit area is also reduced, thus minimizing the inertia-controlled response time of the leaflet during its opening and closing actions; and the diffusion of nutrient into subsequent tissue deposits is hindered to a minimum extent. Moreover the use of more-or-less balanced structural crimp is preferred because it gives a uniform surface contour and hence a tissue deposit with a more uniform thickness. For these reasons it is desired to impose a limit on the level of twist.

Defining the yarn cross-section "aspect ratio" as the ratio of the width of the yarn to its thickness, experience has indicated that acceptable fabric geometries are obtained for aspect ratios greater than 2.0. A yarn having this aspect ratio, comprising "n" filaments arranged in "a" rows has a thickness of "ad" and a width nd/a twice that value, from which it may be derived that for a fabric of balanced structural crimp configuration, the upper limiting fabric thickness would be $(2n)^{\frac{1}{2}}d$. In general, fabrics with thicknesses lying in the lower and central portions of the range defined by expression (1) are preferred.

If there are fewer than eight filaments per yarn, including the case of monofilament yarns, expression (1) is not generally applied as a criterion because the level of twist in fabrics of balanced structural crimp is not important as long as the fabric thickness does not materially exceed the preferred face to face value of 0.06 cm previously mentioned.

An example of a suitable fabric according to expression (1) is an orthogonally woven fabric of identical warp and filling Hytrel yarns, there being 30 filaments per yarn each filament of 20.6 micron diameter. According to expression (1), the lower and upper limiting thicknesses of the fabric are 82 and 160 microns, respectively. The actual measured thickness of the given fabric is 157 microns.

Interfilament and Interyarn Hole Distribution

As described in said copending application, it is preferred to have the lateral dimensions of the foramina, holes or interstitial spacings between the yarns, or between the yarns and filaments, in the range of 20 to 40 microns. In particular, it is preferred that at least 50 percent of the superficial area of at least one face of the fabric contains a substantially uniform distribution of foramina having a maximum lateral aperture dimension of 40 microns. This imposes certain requirements upon "N," defined as the number of yarns per cm. of width in the fabric, as shown by the following expression:

$$\frac{1}{cb + bd} < N < \frac{1}{c + bd} \quad (2)$$

in which "c" is defined as the average hole diameter and preferably lies in the range between $20 \times 10^{-4}$ cm and $40 \times 10^{-4}$ cm, "d" is the filament diameter, and "b" is the number of filaments per row in each yarn. The maximum value in equation (2) is determined by the case in which the only appreciable apertures through the fabric are the spaces between the yarns, the filaments in each yarn being in close side-by-side relationship. The minimum value is determined by the case in which the filaments of the yarns are separated to an extent sufficient to make the apertures between the yarns no greater than those between the respective filaments of each yarn.

Figure 11:
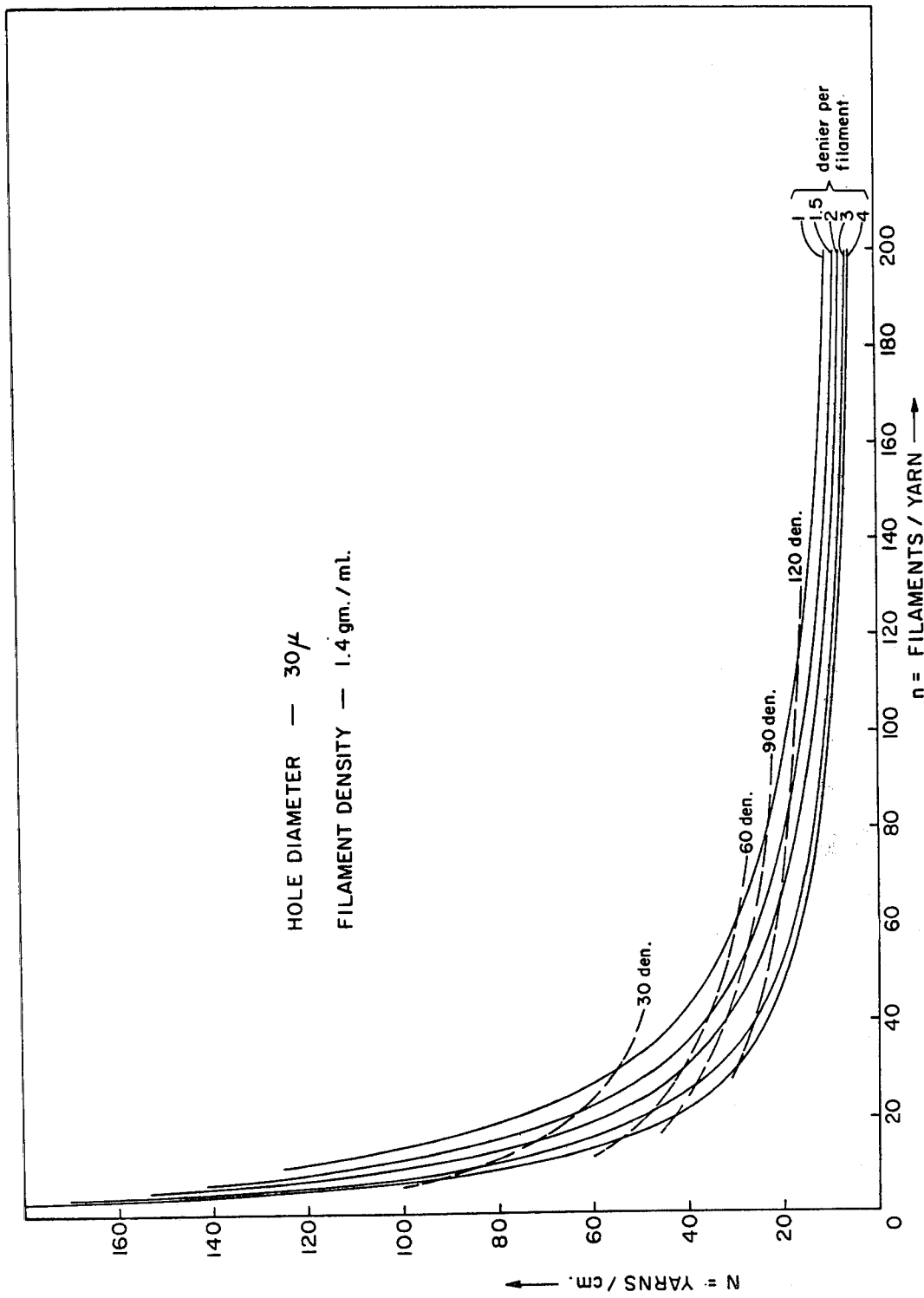
FIG. 11 is a set of typical design graphs used for selection of the appropriate combinations of yarns per unit of fabric width, denier, and number of filaments per yarn, thus taking into account the filament densities and diameters to achieve the desired hole dimensions, that is, the aperture dimensions of the foramina.

When a fabric is to undergo fiber redistribution (spreading) in the finishing processes, then the minimum limiting value in expression (2) can be used as a guide to the type of fabric structure that can be manipulated from some starting configuration to the final desired geometry. When the fabric is intended for use in the as-woven consolidated configuration, with little or no filament redistribution, the maximum value can be used to give the specification of the woven fabric. It is convenient in these latter cases to produce design graphs that embody the analytical relationship, cast in a form suitable for direct use. This is shown in FIG. 11, for example, which shows a series of graphs based on fabrics in which the yarns are in the consolidated, two layer configuration (a=2), with hole diameters of 30 microns, the filament density being 1.4 gm/ml. Similar graphs can be constructed for other yarns and also for other weave pattern geometries.

The graphs shown in broken lines in FIG. 11 show, for yarns of 30, 60, 90 and 120 denier, the value of "N" for each value of "n". The graphs shown in solid lines show, for yarns having 1, 1.5, 2, 3 and 4 denier per filament, the value "N" for each value of "n".

An example of a numerical calculation using the upper limit value in expression (2) is given below for the Hytrel fabric described above having 30 filaments per yarn, each filament of 20.6 microns. This fabric is designed to be used without any subsequent filament redistribution; therefore, all the effective interstitial holes are between yarns, which are themselves organized into approximate three-layer configurations (a=3). In this case, b=30/3=10; d=20.6 microns, and "N", the design threads per unit length for 30 micron holes is given by:

$$N = \frac{1}{30 \times 10^{-4} + 10 \times 20.6 \times 10^{-4}} = 42.4/cm \quad (3)$$

and fabric woven to this specification has a structure in which most of the interyarn spaces are approximately 30 microns in extent.

Flexural Rigidity

It has been pointed out that flexural rigidity of the fabric should be held to a minimum. A mathematical analysis of this property takes into account the Young's modulus "E" of the material, the second moment of area "$I_f$" of the cross section of a fiber, and the effective number of rows of fibers in the yarn. The general formula for the flexural rigidity "$G_f$" of a single fiber is $$G_f = EI_f \quad (4)$$

For the case where the "n" fibers in a yarn are all completely free to move within the cross section the value $G_f$ in equation (4) multiplied by "n" would equal the flexural rigidity of a yarn. On the other hand, such complete freedom does not exist in a prosthetic implant because the fibers have a tissue deposited thereon and this may lead to a minimal to maximal increase in fiber restraint and stiffening of the fabric. In the worst case, if the restraint on the fibers were complete such that they were maintained at all times during bending in a configuration of "a" rows of "b" filaments per row with the neutral plane for bending being at the innermost row, it may be derived that the stiffness would be increased by the following factor $f_s$:

$$f_s = \frac{2(2a^2 + 1)}{3} \quad (5)$$

over the value given above for the case where the fibers are completely free. Expression (5) shows that rigidity increases rapidly with increases in "a". Thus if "a" were "3", the maximum stiffening effect that could be imposed in theory upon the fibers would be approximately one order of magnitude over the completely free case. In practice, however, the tissue actually formed does not have the maximum stiffening effect, and it has been found that the value of "a" may be as high as six without an undesirable stiffening effect. As a more practical measure, it is preferred to establish as a criterion that the yarns have a minor axis (thickness) that is no more than six times the average filament diameter "d", producing a maximum fabric thickness of 12d.

Reverting to the previously-given example of a Hytrel fabric having 30 filaments per yarn, each filament of 20.6 microns, the measured fabric thickness of 157 microns is well under the limit of 12d=247.2 microns established by the criterion for flexural rigidity.

Tensile Compliance

The "N" yarns per unit of width in the fabric, each yarn being composed of "n" filaments, must be such as to provide a tensile strength and modulus approximating those of the natural valve leaflet, described above. This places restraints on the available material and techniques. One centimeter width of artificial leaflet material will contain Nn filaments, using the nomenclature defined above, and will have an effective cross-sectional area of $(Nn\pi d^2)/4$ sq cm. If the tensile modulus of the fiber material is E gm/cm$^2$ then the modulus of the fabric in gm/cm width will be $E_f=(ENn\pi d^2)/4$. Most conventional textile materials have tensile moduli that fall in the range 0.4 to $1.0 \times 10^6$ p.s.i., and are at least two orders of magnitude stiffer than is required to match the stiffness of the heart valve material at maximum stress, and several thousand times stiffer than the heart valve material at low stress levels. There are two useful approaches to the realization of low tensile modulus: in the first approach described in said copending application, excess filament length is introduced into the fabric in the form of crimp. In the second approach described in the present application, low-modulus elastomeric materials are used as the fiber material, and the matching is achieved by means of an overall reduction in the slope of the stress-strain characteristic. Using elastomeric materials of inherently low modulus, no crimping except for structural crimp resulting from fabric production itself is needed, and the fabric is geometrically simpler to model.

Several low modulus elastomeric materials, identified above, have been examined for their mechanical suitability for the leaflet application. These were spun into yarns with various filament diameters and deniers and their tensile behavior was measured. Data on a selection of these materials is given in Table 1 below.

TABLE 1

| TENSILE PROPERTIES OF LOW MODULUS ELASTOMERIC YARNS | | | | |
|---|---|---|---|---|
| (1) Fabric Material | (2) Yarn Denier | (3) No. of Filaments | (4) Filament Diameter,μ | (5) Initial Yarn Tensile Modulus (gm/den) |
| Pellethane | 113 | 30 | 21.8 | 0.09 |
| Silicone | 105 | 30 | 23.8 | 1.14 |
| Arnitel | 81 | 30 | 18.7 | 4.44 |
| Hytrel | 91 | 30 | 20.4 | 0.70 |
| Hytrel | 91 | 30 | 19.5 | 0.70 |
| Hytrel | 71 | 30 | 16.8 | 0.63 |
| PBT | 210 | 30 | 26.8 | 6.9 |
| PBT | 62 | 30 | 16.0 | 7.4 |

In Table 1, "Silicone" refers to the thermoplastic silicone block copolymer previously identified, and "PBT" refers to polybutylene terephthalate, also previously identified. The first listed Hytrel example having a filament diameter of 20.4 microns is the same yarn incorporated in the fabric example previously discussed, having 30 filaments per yarn, although the measurement in the fabric gave a somewhat higher filament diameter reading of 20.6 microns.

Fabrics woven to have desirable tissue reactions have holes that generally fall within the range 20 to 40 microns, as stated above. Preferably, at least 50 percent of the superficial area of at least one face of the sheet material contains a substantially uniform distribution of foramina having a maximum lateral aperture dimension of 40 microns. This requirement is satisfied for the yarns described in Table 1 by incorporating them into fabrics with a yarn density "N" of approximately 40 yarns/cm.

The modulus of the natural leaflet material at the working load level is between approximately 1000 and 3600 gms/cm width. Any of the materials in Table 1, and others with similar tensile properties, are capable of being incorporated into fabrics that have both suitable geometric configurations and the proper tensile response, within a factor of two of these values.

Table 2 lists actual measurements of three woven fabrics each using the first listed Hytrel yarn in Table 1. The fabrics differed somewhat in the average number of yarns per centimeter and in processing, but all were satisfactory for use in prostheses.

TABLE 2

TENSILE PROPERTIES OF WOVEN HYTREL FABRICS
Average Tensile Modulus
Up to 150 gms/cm Width

| Warp Direction | Filling Direction |
|---|---|
| $0.7 \times 10^3$ | $0.6 \times 10^3$ |
| $0.5 \times 10^3$ | $1.0 \times 10^3$ |
| $0.4 \times 10^3$ | $0.6 \times 10^3$ |

Thus, either by suitable manipulation of the geometric form of the filaments and yarns, or by proper choices of filament tensile modulus, or by a combination of these techniques, it is possible to produce fabrics that have the desired combination of properties for heart valve leaflet applications, and also for other prosthetic and medical applications that demand approximately the same property combination. In general, a fabric having a modulus that does not exceed twice the circumferential tensile modulus of the heart valve leaflet material of 3600 grams/cm width, and is not less than half the radial tensile modulus of 1000 gm/cm width at the working load level of 150 gm/cm width will be adequate, and the mechanics of the valve suggest that the lower the modulus at extremely low levels of strain the better the performance will be. The preferred elastomeric multifilament yarns have an average tensile modulus up to a strain of 10 percent in the range of 0.05 to 5.0 grams per denier, the denier of the filaments being within the range between 0.5 and 20.

What is claimed is:

1. A frame system for a heart valve prosthesis comprising:
   a first frame having at least three generally parallel legs each comprising a pair of rod portions connected at one end and diverging at the other end as lobes respectively connecting with rod portions of others of said legs, the lobes forming an aperture therebetween, said legs being adapted to receive the margin of a valve leaflet between the rod portions thereof, whereby said leaflet may be secured to two adjacent legs and the interconnecting lobe so as to have a free edge extending between said adjacent legs; and a second frame adapted to nest with said first frame comprising a rod formed in a closed loop to be substantially congruent with each of said interconnecting lobes between the points of divergence at said other ends of each of said pairs of rod portions, whereby said leaflet may be secured to a lobe by passing it between said frames.

2. A frame system as set forth in claim 1 wherein said legs are equidistant.

3. A heart valve prosthesis comprising:
   a first frame having at least three generally parallel legs each comprising a pair of rod portions connected at one end and diverging at the other end as lobes respectively connecting with rod portions of others of said legs, the lobes forming an aperture therebetween,
   a plurality of flexible leaflets each inserted between the rod portions of two adjacent legs of said first frame, secured to said legs and the interconnecting lobe and having a free edge extending between said adjacent legs, the free edges of said leaflets being deflectable into mutual contact for sealing said aperture, and
   a second frame comprising a rod formed in a closed loop to be substantially congruent with said interconnecting lobes between the points of divergence at said other ends of each of said pairs of rod portions, the leaflets being secured to the lobes by passing them between said frames.

4. A heart valve prosthesis as set forth in claim 3 wherein said leaflets are constituted of fabric.

5. A heart valve prosthesis as set forth in claim 3 wherein each of said leaflets consists essentially of a textile of filaments, each leaflet being sealed to the frames externally of the aperture by adhesive applied along the lines of juncture of each pair of leaflets where they enter between each pair of rod portions, and along said lobes where each leaflet passes between said frames.

6. A heart valve prosthesis as set forth in claim 3 wherein said legs are equidistant.

* * * * *